(12) United States Patent
Te Velde et al.

(10) Patent No.: US 11,337,675 B2
(45) Date of Patent: May 24, 2022

(54) SKIN-MOUNTABLE DEVICE AND MOUNTING METHOD

(71) Applicant: KONINKLIJKE PHILIPS N.V., Eindhoven (NL)

(72) Inventors: Mart Kornelis-Jan Te Velde, Helmond (NL); Paul Jean Geelen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 192 days.

(21) Appl. No.: 16/633,226

(22) PCT Filed: Jul. 18, 2018

(86) PCT No.: PCT/EP2018/069453
§ 371 (c)(1),
(2) Date: Jan. 23, 2020

(87) PCT Pub. No.: WO2019/020441
PCT Pub. Date: Jan. 31, 2019

(65) Prior Publication Data
US 2020/0178932 A1 Jun. 11, 2020

(30) Foreign Application Priority Data
Jul. 26, 2017 (EP) .................................. 17183304

(51) Int. Cl.
*A61B 8/00* (2006.01)
*A61B 5/00* (2006.01)
*A61B 5/259* (2021.01)

(52) U.S. Cl.
CPC ............ *A61B 8/4236* (2013.01); *A61B 5/259* (2021.01); *A61B 5/68335* (2017.08); *A61B 8/4281* (2013.01)

(58) Field of Classification Search
CPC .. A61B 8/4236; A61B 5/6832; A61B 5/68335
See application file for complete search history.

(56) References Cited

U.S. PATENT DOCUMENTS

2009/0004422 A1  1/2009 Bartusiak
2010/0022888 A1* 1/2010 George ............... A61B 8/4209
                                                       600/459

(Continued)

FOREIGN PATENT DOCUMENTS

WO  2011163570 A2  12/2011
WO  2013059600 A1   4/2013
WO  2015174999 A1  11/2015

OTHER PUBLICATIONS

International Search Report and Written Opinion, International Application No. PCT/EP2018/069453, dated Oct. 25, 2018.

(Continued)

*Primary Examiner* — Boniface Ngathi N

(57) ABSTRACT

A skin-mountable device (10) is disclosed comprising a surface (11) carrying an adhesive layer (20) for adhering the device to a skin region (1) and a removable non-adhesive cover layer (30) shaped as a loop having a first loop portion (31) covering the entire adhesive layer and a second loop portion (35) returning over the first loop portion, the second loop portion containing a pull tab (37) for pulling the cover layer from the adhesive layer when the skin-mountable device is positioned on said skin region. Also disclosed is a method of affixing such a skin-mountable device (10) to a skin region (1).

20 Claims, 6 Drawing Sheets

(56) References Cited

U.S. PATENT DOCUMENTS

| | | |
|---|---|---|
| 2010/0098846 A1* | 4/2010 | Ding .................. C09J 7/38 427/207.1 |
| 2011/0165529 A1 | 7/2011 | Murphy et al. |
| 2011/0166529 A1 | 7/2011 | Holmes |
| 2015/0045628 A1 | 2/2015 | Moghadam et al. |
| 2020/0015780 A1 | 1/2020 | Geelen et al. |

OTHER PUBLICATIONS

"VitalPatch", VitalConnect, https://vitalconnect.com/solutions/vitalpatch/, Accessed Jan. 20, 2020.

Captain, S., "This Little Patch Can Save Patients from Impending Heart Attacks", https://www.fastcompany.com/3056952/this-little-patch-can-save-patients-from-impending-heart-attacks, Mar. 2, 2016.

\* cited by examiner

SKIN-MOUNTABLE DEVICE AND MOUNTING METHOD

This application is the U.S. National Phase application under 35 U.S.C. § 371 of International Application No. PCT/EP2018/069453, filed on 18 Jul. 2018, which claims the benefit of European Application Serial No. 17183304.9, filed 26 Jul. 2017. These applications are hereby incorporated by reference herein.

FIELD OF THE INVENTION

The present invention relates to a skin-mountable device comprising a surface carrying an adhesive layer for adhering the device to a skin region and a removable non-adhesive cover layer containing a pull tab extending beyond said surface for pulling the cover layer from the adhesive layer.

The present invention further relates to a method for affixing such a skin-mountable device to the skin region.

BACKGROUND OF THE INVENTION

Nowadays, many devices exist that are to be worn against a portion of the skin of its wearer. Such devices include wearable medical devices or wearable holders for medical devices, but are not limited thereto. For many of such wearable or skin-mountable devices, it may be undesirable to attach the device to the skin of its wearer using a strap or the like, as such a strap may be uncomfortable to the wearer, or it may be unfeasible to attach the device to the skin of its wearer using such a strap as the shape of the body region precludes the device from being kept in position thereon with a strap or the like.

For this reason, skin-mountable devices have been introduced that carry an adhesive layer on a contact surface with such a body region, such that the device can be attached, i.e. adhered, to most body regions without having the potential discomfort of a strap or the like being used as a fastener of the device. For example, US 2015/0045628 A1 discloses a wireless sensor device comprising a housing unit and a patch coupled to the housing unit, wherein the patch includes a removable adhesive, e.g. a plurality of removable adhesive layers such that the patch is repositionable.

However, such skin-mountable devices are not without problems. Firstly, the adhesive layer is typically protected by a non-adhesive layer such as a tape liner, which needs to be removed prior to positioning the skin-mountable device on the region of interest of the skin of its wearer. This renders the contact surface of the skin-mountable device adhesive, such that it becomes cumbersome to reposition the skin-mountable device if it adheres to a skin region other than the intended skin region onto which it is to be mounted, i.e. is incorrectly aligned with this intended skin region. This therefore can easily lead to incorrectly positioned devices, which for example can compromise the functioning of the device where the device implements a medical imaging, monitoring or sensing function or is a holder for a device implementing a medical imaging, monitoring or sensing function, as the device is misaligned with the skin region of interest.

Moreover, such a skin region of interest may carry a substance to improve a signal exchange between the device and the skin region of interest, such as an acoustic contact gel between an ultrasound probe and the skin. Subsequent positioning of the skin-mountable device may be problematic as the substance present on the skin region can interfere with the adhesion of the skin-mountable device to the skin region.

SUMMARY OF THE INVENTION

The present invention seeks to provide a skin-mountable device that can be positioned on an intended skin region and addresses at least some of the aforementioned problems.

The present invention further seeks to provide a method of affixing such a skin-mountable device to a skin region.

According to an aspect, there is provided a skin-mountable device comprising a surface carrying an adhesive layer for adhering the device to a skin region and a removable non-adhesive cover layer shaped as a loop having a first loop portion covering the entire adhesive layer and a second loop portion connected to the first loop portion by a loop return and returning over the first loop portion, the second loop portion containing a pull tab opposing said loop return and extending beyond said surface.

The provision of such a looped cover layer, e.g. a tape liner or the like, allows for the skin-mountable device to be correctly positioned on the skin region of interest without exposure of its adhesive layer, thereby avoiding the device 'sticking' to an undesired region of the skin. Following the correct positioning of the skin-mountable device in its non-adhesive state, the adhesive layer can be exposed upon removal of the looped cover layer by pulling of the pull tab whilst the skin-mountable device is in-situ, thereby exposing the adhesive layer and affixing the skin-mountable device to the intended skin region. The provision of a looped cover layer has the further advantage over a single layered cover layer that the friction forces acting upon the cover layer upon its removal are reduced, thereby reducing the risk that the skin-mountable device is repositioned, i.e. misaligned, when the cover layer is pulled from in between the skin-mountable device and the skin region of interest.

In an embodiment, the skin-mountable device further comprises at least one adhesive region in between the first loop portion and the second loop portion to secure the second loop portion against the first loop portion. This for example may improve the ease of handling of the skin-mountable device due to the fact that the loop of the cover layer is kept in place by the at least one adhesive region, such that a user does not have to restore (e.g. refold) the loop when positioning the skin-mountable device onto the skin region of interest.

For example, the at least one adhesive region may comprise a plurality of adhesive dots spaced apart in between the first and second loop portions, which secures the second loop portion against the first loop portion in an effective manner whilst limiting the force required to disrupt the adhesion between the first and second loop portions provided by the at least one adhesive region due to the limited size of such adhesive dots.

It is furthermore preferred that the at least one adhesive region is made of a low-tack adhesive such that it breaks (de-adheres) when the cover layer is pulled from the adhesive layer, e.g. a low-tack polymer adhesive, that easily releases of its carrying surface from a bonding surface upon the application of a modest force thereon.

In a further embodiment, the cover layer comprises a cleaning portion arranged to clean the skin region when the cover layer is pulled from the adhesive layer. This arrangement cleans the skin region of interest prior to establishing contact between the adhesive layer and this skin region when the cover layer is pulled from between the adhesive layer and this skin region due to the cleaning portion being pulled through this contact region. This therefore improves the adhesive contact between the skin-mountable device and the skin region of interest. The cleaning portion may comprise the second loop portion and/or may comprise a third loop portion in between the first loop portion and the second loop portion for example.

The cleaning portion may carry a cleaning material (or disinfectant, or sterilizer) for cleaning (or disinfecting, or sterilizing) said skin region. Alternatively, the cleaning portion may be made of a cleaning material for cleaning said skin region. The cleaning material in example embodiments is an abrasive or absorbent material such as a non-woven fabric, e.g. a cleaning tissue or the like.

In an embodiment, the skin-mountable device further comprises at least one adhesive further region adhering the third loop portion to the skin-mountable device to secure the third loop portion against the skin-mountable device for ease of handling. Alternatively or additionally, the skin-mountable device may further comprise a channel housing the third loop portion for such ease of handling.

The adhesive layer may be realized using any suitable adhesive, such as a medical grade pressure sensitive adhesive (PSA) such as a silicone PSA. In an example embodiment, the adhesive layer comprises an adhesive tape.

In a first set of embodiments, the skin-mountable device is a wearable medical device such as a wearable sensor device or the like.

In a second set of embodiments, the skin-mountable device is a holder for an ultrasound probe such that the ultrasound probe can be easily positioned on the desired skin region, e.g. for imaging or treating a body portion below the skin region with ultrasound waves. Also provided is an ultrasound probe arrangement comprising such a holder and the ultrasound probe.

According to a further aspect, there is provided a method of affixing a skin-mountable device according to any of the herein described embodiments to a skin region, the method comprising positioning the skin-mountable device on the skin region; pulling the pull tab of the cover layer to remove the cover layer from in between the adhesive layer and the skin region; and pressing the skin-mountable device onto the skin region to adhere the skin-mountable device to the skin region with the adhesive layer. This method allows for the precise positioning of the skin-mountable device due to its non-adhesive contact surface during the positioning, whilst the looped cover layer can be easily removed to expose the adhesive layer and affix the skin-mountable device to the skin region of interest by pressing the skin-mountable device onto this skin region. The easy removal of the looped cover layer reduces the risk that the skin-mountable device is repositioned (i.e. shifted sideways in the direction in which the cover layer is pulled from in between the skin-mountable device and the skin region of interest) during its removal.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
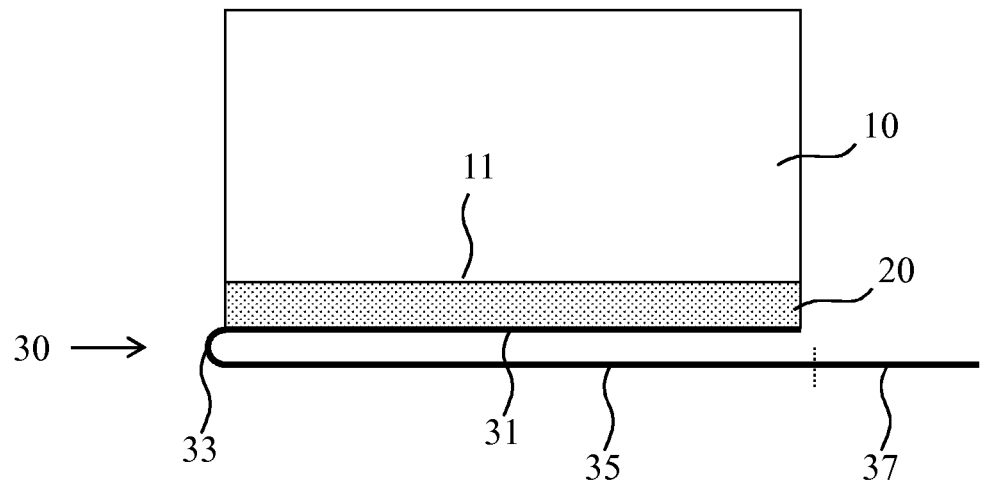
FIG. 1 schematically depicts a cross-sectional view of a skin-mountable device according to an embodiment.

It should be understood that the Figures are merely schematic and are not drawn to scale. It should also be understood that the same reference numerals are used throughout the Figures to indicate the same or similar parts.

FIG. 1 schematically depicts a skin-mountable device 10 according to an example embodiment of the present invention. The skin mountable device 10 may be a wearable device, such as a wearable medical device or a holder for a medical device as will be explained in further detail below. Where the skin-mountable device 10 is a wearable medical device, the skin-mountable device 10 may comprise functionality to sense or otherwise monitor a bodily function of the wearer of such a device. For instance, the skin-mountable device 10 may be a wearable patch including a sensing electrode arrangement such as an ECG electrode arrangement, a sensor device such as a blood glucose monitoring device, an ultrasound based sensor for measuring blood flow or heart rate based on single piezo transducers, sensors with capacitive micromachined ultrasound transducer (cMUT) based ultrasound transducers for imaging or blood flow monitoring, an accelerometer to track patient activity, a wearable blood pressure sensor or photoplethysmogram (PPG) sensor, and so on. Many other examples will be immediately apparent to the skilled person.

The skin-mountable device 10 may be connected to a further device for registering and/or recording data generated with the skin-mountable device 10. Such a connection may be a wired connection in which case the skin-mountable device 10 includes a cable, wire or the like for connecting the skin-mountable device 10 to the further device or alternatively such a connection may be a wireless connection in which case the skin live mountable device 10 includes a wireless communication module for wirelessly communicating with the further device. Such wireless communication may employ any suitable wireless communication standard such as Wi-Fi, Bluetooth, NFC, GMS, UMTS, 3G, 4G, 5G as non-limiting examples. Other suitable wireless communication standards will be immediately apparent to the skilled person.

The skin-mountable device 10 may further comprise active circuitry such as a processor for processing signals generated with the skin-mountable device 10. It should be understood that the actual embodiment of the skin-mountable device 10 is not particularly limited and that any type of skin-mountable device 10 may be used in according with the teachings of the present invention.

The skin-mountable device 10 comprises a contact surface 11 to be brought into contact with the skin of its intended wearer, e.g. a patient in case of a wearable medical device or wearable holder of such a device. The contact surface 11 may have any suitable shape, e.g. a planar shape or a contoured shape, which contoured shape may match the shape of a body portion of the intended wearer onto which the skin-mountable device 10 is to be mounted. The contact surface 11 carries an adhesive layer 20 arranged to adhere the skin-mountable device 10 to an intended skin region of the intended wearer of the skin-mountable device 10. Any suitable adhesive may be used for such an adhesive layer 20. For example, the adhesive layer 20 may be formed of a layer of sticky tape attached to the contact surface 11. Alternatively, the adhesive layer 20 may be formed of a pressure sensitive adhesive such as a pressure sensitive silicone adhesive, an acrylic based adhesive or a polyurethane based adhesive. Many more suitable adhesives will be immediately apparent to the skilled person.

In order to protect the adhesive layer 20 from premature exposure, a cover layer 30 is arranged over the adhesive layer 20. In accordance with embodiments of the present invention, the cover layer 30 is shaped such that the skin-mountable device 10 can be positioned on an intended region of the skin of its intended wearer, e.g. a patient in case of a wearable medical device or wearable holder thereof, whilst the cover layer 30 is still in place. More specifically, the cover layer 30 is shaped such that it can be easily removed from in between the skin-mountable device 10 and the intended region of the skin of its intended wearer without disturbing the positioning of the skin-mountable device 10 on the intended region of the skin.

To this end, the cover layer 30 is shaped as a loop having a first loop portion 31 covering the adhesive layer 20 and a second loop portion 35 returning over the first loop portion 31 via a loop return 33 connecting the first loop portion 31 to the second loop portion 35. The second loop portion 35 further comprises a pull tab 37, which may be a portion of the second loop portion 35 extending beyond the perimeter of the skin-mountable device 10 for pulling the cover layer 30 from in between the adhesive layer 20 of the skin-mountable device 10 and the intended region of the skin of its intended wearer onto which the skin-mountable device 10 is positioned, as will be explained in further detail below.

The cover layer 30 may be made of any suitable non-adhesive material. For example the cover layer 30 may be a release liner or the like made of a thin film of a non-adhesive release material, e.g. a paper-based material such as super calendared Kraft paper, glassine, clay coated Kraft paper, machine finished Kraft paper, machine glazed paper or a plastic film based material such a biaxially oriented polyethylene film, a biaxially oriented polypropylene film or any other suitable polyolefin such as high-density polyethylene, low-density polyethylene and polypropylene plastic resins, or composite materials such as polymer coated Kraft papers.

Furthermore, it is noted that in the context of the present application, where reference is made to a looped cover layer 30, this is intended to include a layer 30 that is folded such that a first fold portion (i.e. the first loop portion 31) of the cover layer 30 contacts the adhesive layer 20 of the skin-mountable device 10 and a second fold portion (i.e. the first loop portion 35) of the cover layer 30 covers the first fold portion such that when the skin-mountable device 10 is positioned on the skin of its intended wearer the second fold portion is located in between the first fold portion and the skin of the intended wearer.

It may be desirable to secure the second loop portion 35 against the first loop portion 31 to ensure that the looped arrangement of the cover layer 30 stays intact when the skin-mountable device 10 is being handled, e.g. is positioned onto the intended region of the skin of its intended wearer. This avoids the risk of the loop unfolding during such handling, which is undesirable due to the fact that removal of the cover layer 30 after the skin-mountable device 10 is positioned on this intended skin region is more cumbersome, i.e. requires more force, when the loop of the cover layer 30 has unfolded, thereby increasing the risk of the positioning of the skin-mountable device 10 on this intended skin region becoming disturbed, i.e. the skin-mountable device 10 becoming displaced during the release of the cover layer 30 from in between the skin-mountable device 10 and the intended skin region.

Figure 2:
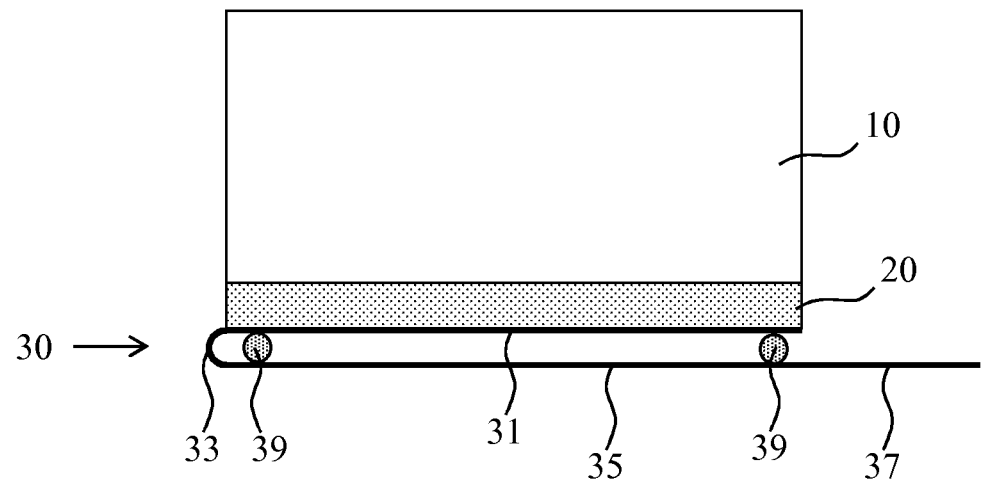
FIG. 2 schematically depicts a cross-sectional view of a skin-mountable device according to another embodiment.

FIG. 2 schematically depicts an example embodiment of the skin-mountable device 10 in which an adhesive region 39 is provided in between the first loop portion 31 and the second loop portion 35 to secure the second loop portion 35 against the first loop portion 31. The adhesive region 39 may be embodied by a plurality of adhesive dots as shown in FIG. 2 although other suitable arrangements for adhering the first loop portion 31 to the second loop portion 35 of the cover layer 30 will be immediately apparent to the skilled person.

The adhesive region 39 preferably is made of a low-tack adhesive such that when the cover layer 30 is pulled from in between the skin-mountable device 10 and the intended skin region, the adhesion of the first loop portion 31 to the second loop portion 35 is broken such that the second loop portion 35 can be displaced independently of the first loop portion 31 during the removal of the cover layer 30. Such low-tack adhesives are well-known per se; as a non-limiting example an acrylate-copolymer adhesive such as acrylate-copolymer (micro)spheres, as for example described in U.S. Pat. No. 3,691,140, is mentioned although it should be understood that any suitable low-tack adhesive may be used for this purpose such as synthetic rubber adhesives, silicone pressure sensitive adhesives and soft silicone gel adhesives for example.

Figure 3:
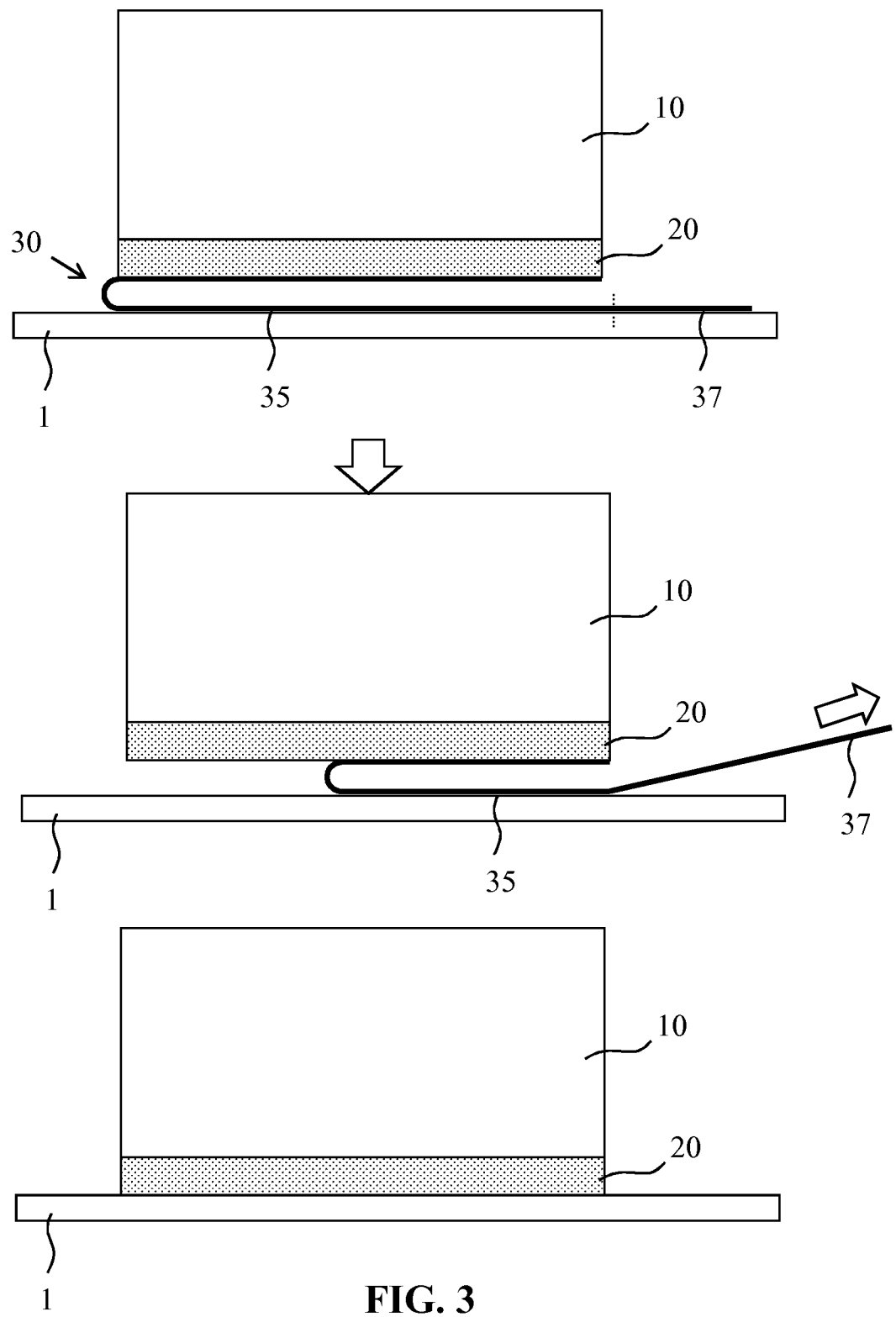
FIG. 3 schematically depicts an example embodiment of a method of affixing such a skin-mountable device to a skin region of interest.

FIG. 3 schematically depicts an example method of affixing, i.e. adhering, such a skin-mountable device 10 to an intended skin region 1 of its intended wearer. In a first step (top pane), the skin-mountable device 10 is positioned on the intended region of the skin 1 of its intended wearer such that the adhesive layer 20 faces the intended region with the looped cover layer 30 located in between the adhesive layer 20 and this intended region. Next, the looped cover layer 30 is pulled using the pull tab 37 from in between the adhesive layer 20 and this intended region (middle pane) whilst pressing the skin-mountable device 10 onto the intended region of the skin 1 as indicated by the block arrows. Because the first looped portion 31 and the second looped portion 35 slide along each other whilst the cover layer 30 is being pulled from in between the adhesive layer 20 and the intended region of the skin 1, this leads to a substantially frictionless removal of the cover layer 30, i.e. substantially less friction as in the case of a single cover layer in between the adhesive layer and the intended region of the skin 1, thereby reducing the risk of the positioning of the skin-mountable device 10 onto this intended region being disturbed. Upon complete removal of the cover layer 30 from in between the adhesive layer 20 and the intended region of the skin 1, the skin-mountable device 10 is mounted and adhered to the intended region of the skin 1 (bottom pane).

In some applications, it may be desirable to clean the intended region of the skin 1 prior to adhesion of the skin-mountable device 10 thereto. For example, where the skin-mountable device 10 is a holder for a medical device, such as an ultrasound probe, the skin-mountable device 10 may comprise an aperture extending through the skin-mountable device 10, with the contact surface 11 delimiting this aperture. In such a scenario, the skin-mountable device 10 may be positioned onto the intended region of the skin 1 with the ultrasound probe in situ in the skin-mountable device 10, in which case a contact gel may be provided on the intended region of the skin 1 to be imaged or treated with the ultrasound probe. It is practically impossible to prevent such a contact gel from also covering the part of the skin to be contacted by the contact surface 11 of the skin-mountable device 10, i.e. the region of the skin to which the skin-mountable device 10 is to be adhered. However, cleaning the skin prior to placement of the skin-mountable device 10 thereon is also far from ideal as this typically will also at least partially remove the contact gel from the skin region to be contacted by the ultrasound probe.

Figure 4:
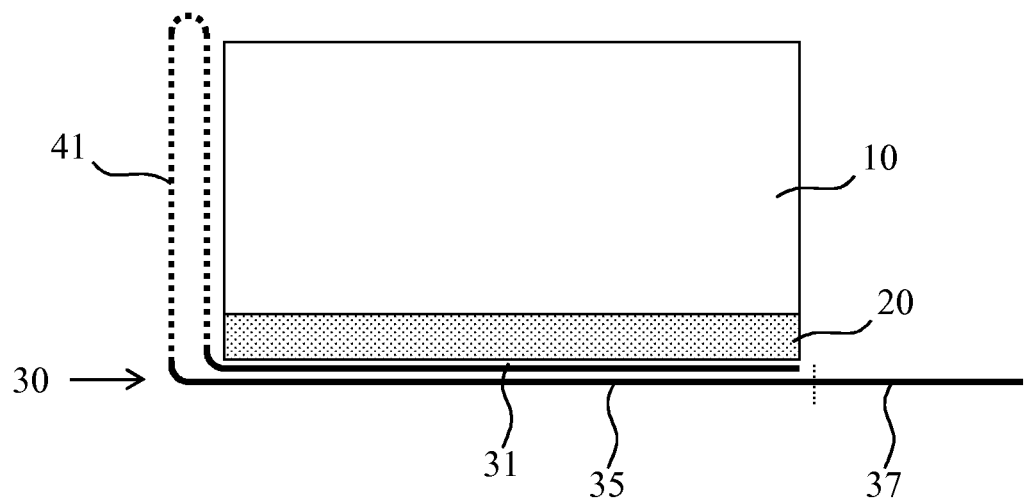
FIG. 4 schematically depicts a cross-sectional view of a skin-mountable device according to a further embodiment.

FIG. 4 schematically depicts a skin-mountable device 10 according to a further embodiment of the present invention in which the looped cover layer 30 includes a third loop portion 41 in between the first loop portion 31 and the second loop portion 35. The third loop portion 41 is made of or carries a cleaning material for cleaning the region of the skin 1 to be contacted by the contact surface 11 of the skin-mountable device 10 carrying the adhesive layer 20. For example, the cleaning material may be a solvent such as isopropyl alcohol or another alcohol-based solvent, an abrasive or absorbent material, e.g. a non-woven fabric, paper tissue, or the like, that wipes clean this region of the skin when the cover layer 30 is pulled from in between the adhesive layer 20 and the intended region of the skin 1 to be contacted by the adhesive layer 20 when pulling the cover layer 30 using the pull tab 37 as previously explained, thereby cleaning this skin region and improving the adhesion between this skin region and the skin-mountable device 10. Consequently, this makes it possible to accurately and securely position the skin-mountable device 10 onto a region of the skin that has been treated with a substance such as a contact gel due to the fact that the substance can be effectively removed from those skin regions to be contacted by the adhesive layer 20.

Alternatively, the third loop portion 41 may be omitted, in which case the second loop portion 35 may be made of or may carry a cleaning material for cleaning the region of the skin 1 to be contacted by the contact surface 11 of the skin-mountable device 10 carrying the adhesive layer 20. In yet a further embodiment, both the second loop portion 35 and the third loop portion 41 may be made of or may carry a cleaning material for cleaning the region of the skin 1 to be contacted by the contact surface 11 of the skin-mountable device 10 carrying the adhesive layer 20. In such an arrangement, the second loop portion 35 and the third loop portion 41 may be made of or may carry the same cleaning material or different cleaning materials, e.g. a solvent and an adsorbent or abrasive material respectively in order to dissolve and subsequently remove pollutants from the skin region of interest.

For the avoidance of doubt, it is noted that such a skin-mountable device 10 is not limited for use in combination with such substances but equally may be used for any type of skin-mountable device 10 simply to clean the intended region of the skin to which the skin-mountable device 10 is to be adhered in order to improve the quality of the adhesion.

Figure 5:
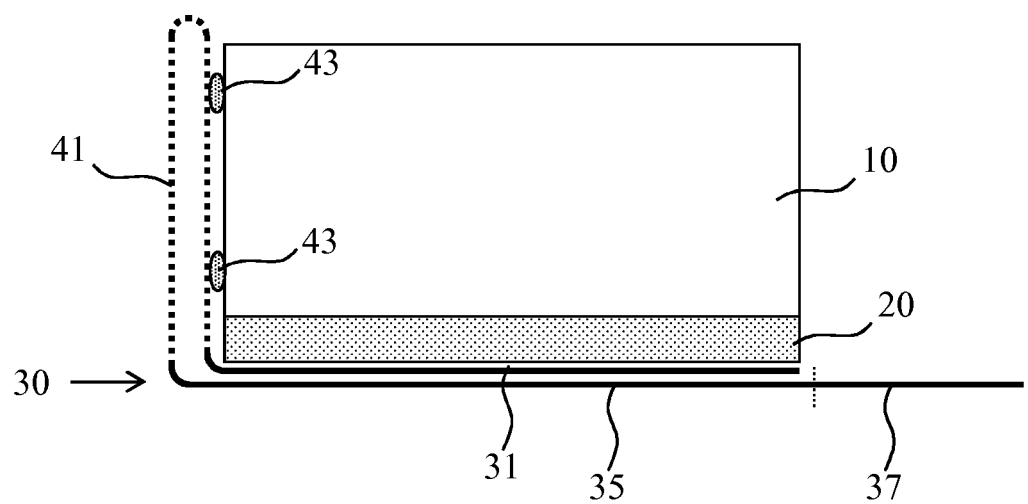
FIG. 5 schematically depicts a cross-sectional view of a skin-mountable device according to still a further embodiment.

FIG. 5 schematically depicts a skin-mountable device 10 according to a yet a further embodiment of the present invention in which the third loop portion 41 is secured against the skin-mountable device 10 with at least one adhesive further region 43, e.g. a plurality of adhesive dots, which as with the at least one adhesive region 39 preferably is made of a weak adhesive such as a low-tack adhesive such that upon pulling the cover layer 30 from in between the adhesive layer 20 of the skin-mountable device 10 and the intended region of the skin 1, the at least one adhesive further region 43 is broken and the third loop portion 41 is released from the skin-mountable device 10. The provision of the at least one adhesive further region 43 in between the third loop portion 41 and the skin-mountable device 10 i.e. its body or housing, ensures that the third loop portion 41 is kept in place when the skin-mountable device 10 is being handled, which improves the ease of handling of the skin-mountable device 10 and reduces the risk that the third loop portion 41 is unintentionally caught by a foreign object, which could damage the cover layer 30 or may at least partially remove the cover layer 30 from the adhesive layer 20.

Figure 6:
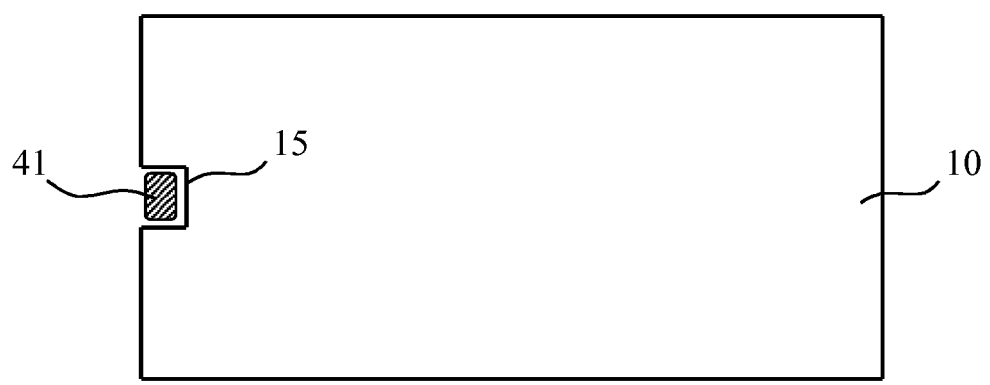
FIG. 6 schematically depicts a top view of a skin-mountable device according to yet a further embodiment.

Alternatively, as schematically depicted in FIG. 6, the skin-mountable device 10 may incorporate a channel 15 in its body or housing into which the third loop portion 41 may be secured to keep it from such accidental damage or disruption. Although not specifically shown in FIG. 6, at least one adhesive further region 43 further may be present in between the third loop portion 41 and the channel 15 to further secure the third loop portion 41 in the channel.

Figure 7:
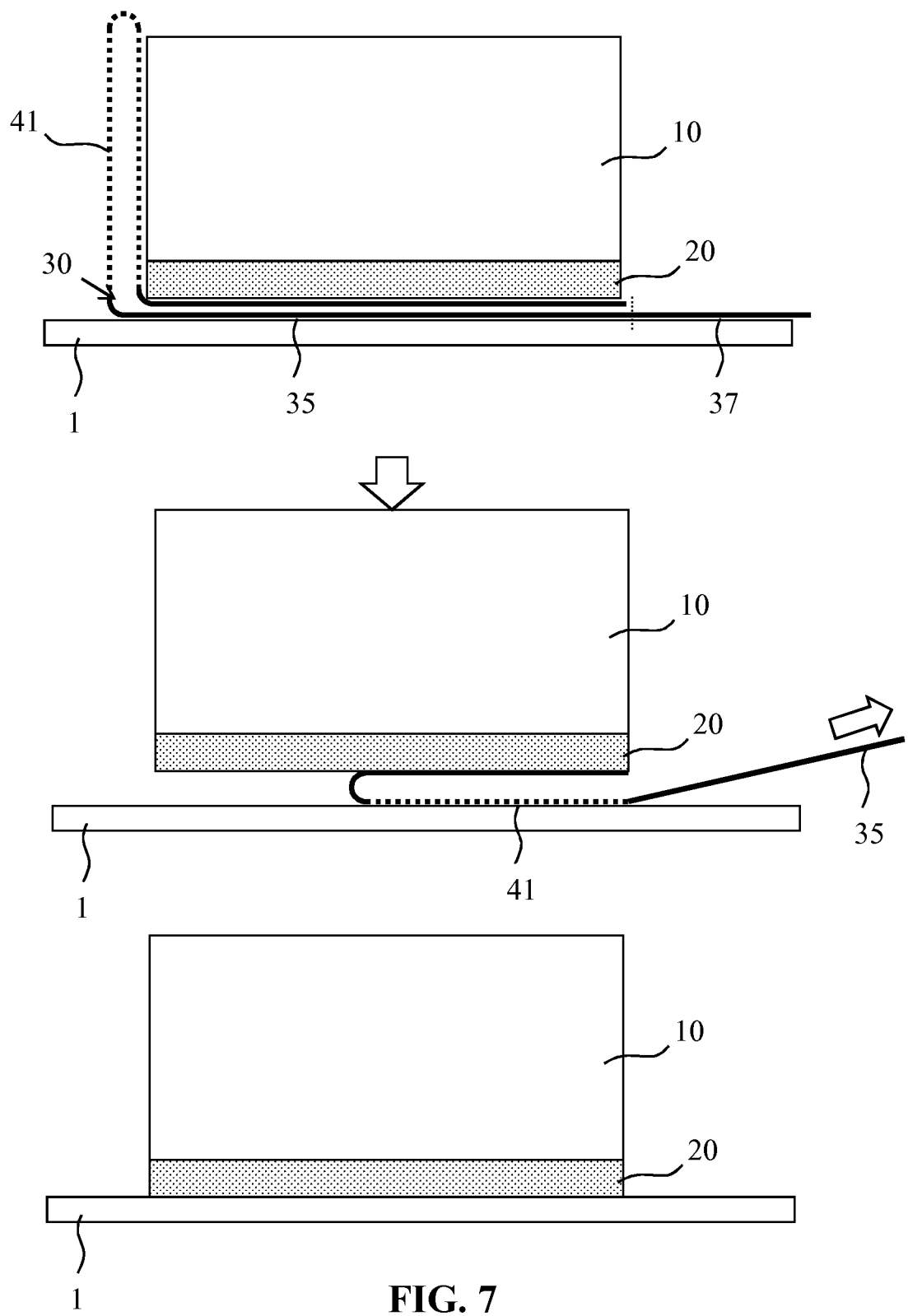
FIG. 7 schematically depicts another example embodiment of a method of affixing such a skin-mountable device to a skin region of interest.

FIG. 7 schematically depicts an example method of affixing, i.e. adhering, such a skin-mountable device 10 to an intended skin region 1 of its intended wearer. In a first step (top pane), the skin-mountable device 10 is positioned on the intended region of the skin 1 of its intended wearer such that the adhesive layer 20 faces the intended region with the looped cover layer 30 located in between the adhesive layer 20 and this intended region. Next, the looped cover layer 30 is pulled using the pull tab 37 from in between the adhesive layer 20 and this intended region (middle pane) whilst pressing the skin-mountable device 10 onto the intended region of the skin 1 as indicated by the block arrows. This pulls the third loop portion 41 over the contact region between the adhesive layer 20 and the skin 1 prior to removing the first loop portion 31 of the cover layer 30 from the adhesive layer such that this contact region is cleaned before it is exposed to the adhesive layer 20 of the skin-mountable device 10. Upon complete removal of the cover layer 30 from in between the adhesive layer 20 and the intended region of the skin 1, the skin-mountable device 10 is mounted and adhered to the intended region of the skin 1 (bottom pane) in a secure manner due to the cleaning of the intended region with the third loop portion 41 of the cover layer 30 before exposing this region to the adhesive layer 20.

Figure 8:
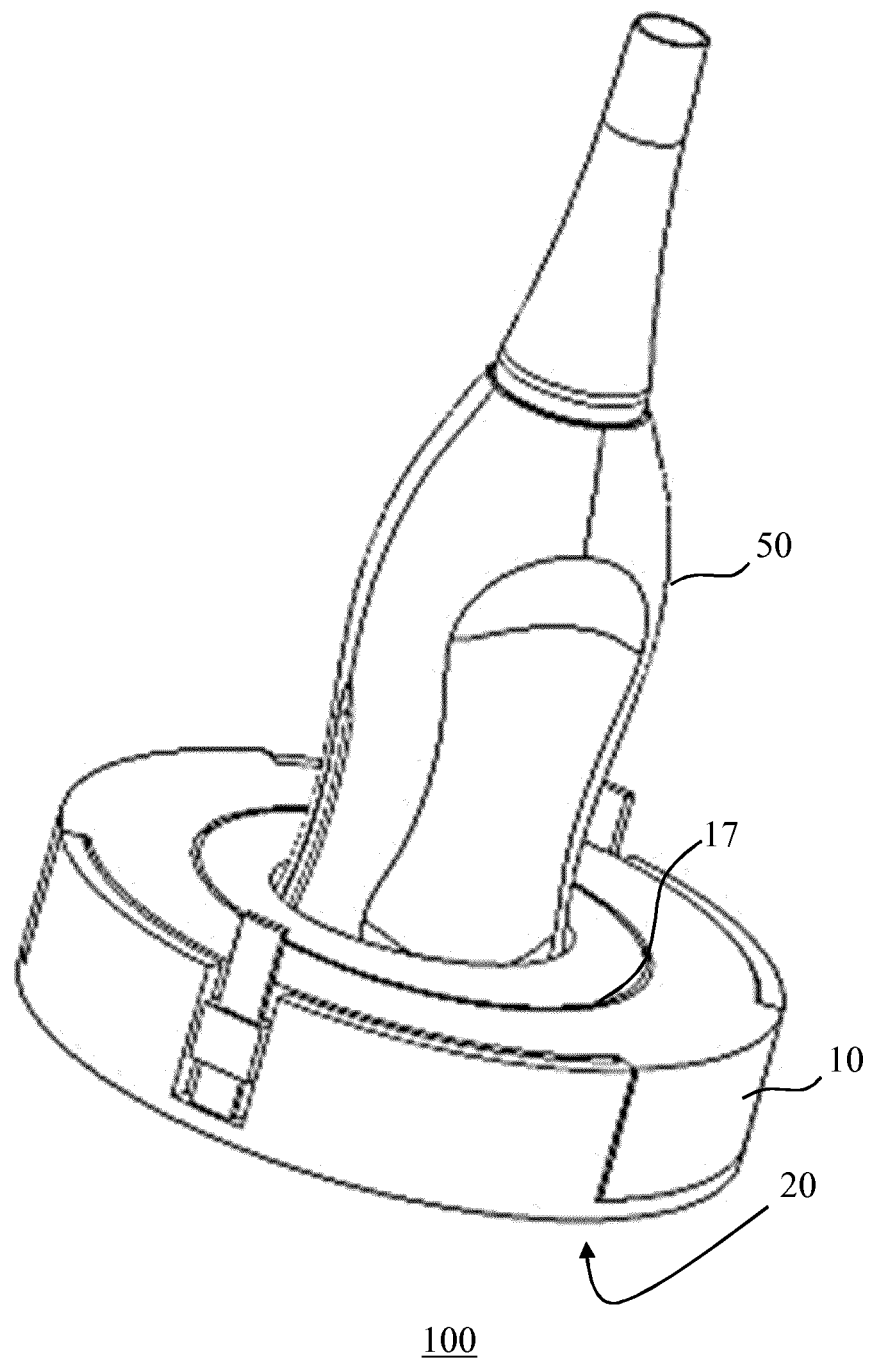
FIG. 8 schematically depicts a perspective view of an ultrasound probe arrangement according to an example embodiment.

FIG. 8 schematically depicts an ultrasound probe arrangement 100 including an ultrasound probe 50 (in the context of this application the ultrasound probe can be a low profile ultrasound based monitoring patch suitable for long term attachment to the skin) and the skin-mountable device 10, here a holder of the ultrasound probe 50 including a mounting aperture 17, which may comprise a swivel arrangement or the like that facilitates movement, e.g. free rotation, of the ultrasound probe within the holder. Such arrangements are well-known per se and are therefore not explained in further detail for the sake of brevity only. The contact surface 11 of the skin-mountable device 10 (not visible in FIG. 8) typically delimits the aperture 17 and carries the adhesive layer 20 such that the skin-mountable device 10 can be affixed to the intended region of the skin as explained in more detail above. Preferably, the cover layer 30 of the skin-mountable device 10 includes the third loop portion 41 such that a contact gel can be applied on the skin region of interest onto which the skin-mountable device 10 is to be placed, with the third loop portion 41 substantially removing the contact gel from the contact region of the skin with the adhesive layer 20 to properly secure the skin-mountable device 10 against the skin of the patient.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A skin-mountable device comprising:
    a surface comprising:
        an adhesive layer for adhering the device to a skin region; and
        a removable non-adhesive cover layer shaped as a loop having a first loop portion covering the entire adhesive layer and a second loop portion connected to the first loop portion by a loop return and returning over the first loop portion, the second loop portion containing a pull tab opposing said loop return and extending beyond said surface,
            wherein the cover layer comprises a cleaning portion arranged to clean the skin region when the cover layer is pulled from the adhesive layer, and
            wherein the cleaning portion comprises at least one of: an abrasive and an absorbent.

2. The skin-mountable device of claim 1, further comprising at least one adhesive region in between the first loop portion and the second loop portion.

3. The skin-mountable device of claim 2, wherein the at least one adhesive region comprises a plurality of adhesive dots.

4. The skin-mountable device of claim 2, wherein the at least one adhesive region is made of a low-tack adhesive such that the at least one adhesive region breaks when the cover layer is pulled from the adhesive layer.

5. The skin mountable device of claim 1, wherein the cleaning portion comprises at least one of the second loop portion and a third loop portion between the first loop portion and the second loop portion.

6. The skin-mountable device of claim 5, further comprising at least one secondary adhesive region adhering the third loop portion to the skin-mountable device.

7. The skin-mountable device of claim 5, further comprising a channel housing the third loop portion.

8. The skin-mountable device of claim 1, wherein the adhesive layer comprises an adhesive tape.

9. The skin-mountable device of claim 1, wherein the skin-mountable device is a wearable medical device.

10. The skin-mountable device of claim 1, wherein the skin-mountable device is a holder for an ultrasound probe.

11. A method of affixing a skin-mountable device to a skin region, the method comprising:
    positioning the skin-mountable device on the skin region, wherein the skin mountable device comprises a surface comprising: an adhesive layer for adhering the device to a skin region; and a removable non-adhesive cover layer shaped as a loop having a first loop portion covering the entire adhesive layer and a second loop portion connected to the first loop portion by a loop return and returning over the first loop portion, the second loop portion containing a pull tab opposing said loop return and extending beyond said surface, wherein the cover layer comprises a cleaning portion arranged to clean the skin region when the cover layer is pulled from the adhesive layer, wherein the cleaning portion comprises at least one of: an abrasive and an absorbent;
    pulling the pull tab of the cover layer to remove the cover layer from in between the adhesive layer and the skin region; and
    pressing the skin-mountable device onto the skin region to adhere the skin-mountable device to the skin region with the adhesive layer.

12. A skin-mountable device comprising:
    a surface comprising:
        an adhesive layer for adhering the device to a skin region; and
        a removable non-adhesive cover layer shaped as a loop having a first loop portion covering the entire adhesive layer and a second loop portion connected to the first loop portion by a loop return and returning over the first loop portion, the second loop portion containing a pull tab opposing said loop return and extending beyond said surface,
            wherein the cover layer comprises a cleaning portion arranged to clean the skin region when the cover layer is pulled from the adhesive layer, and
            wherein the cleaning portion comprises a third loop portion between the first loop portion and the second loop portion.

13. The skin-mountable device of claim 12, further comprising at least one adhesive region in between the first loop portion and the second loop portion.

14. The skin-mountable device of claim 13, wherein the at least one adhesive region comprises a plurality of adhesive dots.

15. The skin-mountable device of claim 13, wherein the at least one adhesive region is made of a low-tack adhesive such that the at least one adhesive region breaks when the cover layer is pulled from the adhesive layer.

16. The skin-mountable device of claim 12, further comprising at least one secondary adhesive region adhering the third loop portion to the skin-mountable device.

17. The skin-mountable device of claim 12, further comprising a channel housing the third loop portion.

18. The skin-mountable device of claim 12, wherein the adhesive layer comprises an adhesive tape.

19. The skin-mountable: device of claim 12, wherein the skin-mountable device is a wearable medical device.

20. The skin-mountable device of claim 12, wherein the skin-mountable device is a holder for an ultrasound probe.

* * * * *